United States Patent
Ruggieri et al.

(10) Patent No.: US 10,144,723 B2
(45) Date of Patent: Dec. 4, 2018

(54) TREATMENT OF SOLID TUMORS BY INHIBITING MRK/ZAK

(71) Applicant: The Feinstein Institute For Medical Research, Manhasset, NY (US)

(72) Inventors: Rosamaria Ruggieri, Roslyn Estates, NY (US); Yousef Al-Abed, Dix Hills, NY (US); Marc Symons, Roslyn Estates, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 15/305,107

(22) PCT Filed: Apr. 21, 2015

(86) PCT No.: PCT/US2015/026744
§ 371 (c)(1),
(2) Date: Oct. 19, 2016

(87) PCT Pub. No.: WO2015/164294
PCT Pub. Date: Oct. 29, 2015

(65) Prior Publication Data
US 2017/0217929 A1    Aug. 3, 2017

Related U.S. Application Data

(60) Provisional application No. 61/982,407, filed on Apr. 22, 2014.

(51) Int. Cl.
| | | |
|---|---|---|
| C07D 401/14 | (2006.01) | |
| A61K 45/06 | (2006.01) | |
| A61K 31/506 | (2006.01) | |
| A61K 41/00 | (2006.01) | |
| A61N 5/10 | (2006.01) | |

(52) U.S. Cl.
CPC ......... *C07D 401/14* (2013.01); *A61K 31/506* (2013.01); *A61K 41/0038* (2013.01); *A61K 45/06* (2013.01); *A61N 5/10* (2013.01); *A61N 2005/1098* (2013.01)

(58) Field of Classification Search
CPC ... C07D 239/02; C07D 401/14; A61K 31/505
USPC ........................................ 544/331; 514/275
See application file for complete search history.

(56) References Cited

FOREIGN PATENT DOCUMENTS

| WO | 2011050319 A2 | 4/2011 |
|---|---|---|
| WO | 2012170976 A2 | 12/2012 |

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Gura et al., Systems for identifying new drugs are often faulty, Science, 278:1041-1042, (1997).*
Johnson et al., Relationships between drug activity in NCI preclinical in vitro and in vivo models and early clinical trials, British Journal of Cancer, 84(10):1424-1431, (2001).*
Simone, Oncology: Introduction, Cecil Textbook of Medicine, 20th Edition, vol. 1, pp. 1004-101 O, (1996).*
Pearce et al., Failure modes in anticancer drug discovery and development, Cancer Drug Design and Discovery Edited by Stephen Neidle, Chapter 18, pp. 424-435 (2008).*
PCT International Search Report and Written Opinion dated Jul. 13, 2015 for PCT International Patent Application No. PCT/US2015/26744, 10 pages.
Ding M et al., entitled "Newly developed strategies for improving sensitivity to radiation by targeting signal pathways in cancer therapy" Cancer Sci, Nov. 2013, vol. 104, No. 11, 1401-1410.
Bloem L J et al., entitled "Tissue Distribution and Functional Expression of a cDNA Encoding a Novel Mixed Lineage Kinase," J Mol Cell Cardiol 33, 1739-1750 (2001).
Gotoh I et al., entitled "Identification and Characterization of a Novel MAP Kinase Kinase Kinase, MLTK," The Journal of Biological Chemistry, vol. 276, No. 6, Issue of Feb. 9, pp. 4276-4286, 2001.
Gross E A., et al., entitled "MRK, a Mixed Lineage Kinase-related Molecule That Plays a Role in γ-Radiation-induced Cell Cycle Arrest," The Journal of Biological Chemistry, vol. 277, No. 16, Issue of Apr. 19, pp. 13873-13882, 2002.
Manley P W et al., entitled "Extended kinase profile and properties of the protein kinase inhibitor nilotinib," Biochimica et Biophysica Acta 1804 (2010) 445-453.

(Continued)

*Primary Examiner* — Deepak R Rao
(74) *Attorney, Agent, or Firm* — Amster, Rothstein & Ebenstein LLP

(57) ABSTRACT

Methods and compounds are described for treating solid tumors, and in particular, malignant, neoplastic solid tumors such as glioblastoma and medulloblastoma, by inhibiting protein kinase MRK/ZAK activity. Also provided are pharmaceutical composition containing a MRK/ZAK inhibitor compound and a pharmaceutically acceptable carrier and a method of sensitizing tumor cells to radiation therapy comprising administering an effective amount of the MRK/ZAK inhibitor compound.

17 Claims, 11 Drawing Sheets

(56) References Cited

OTHER PUBLICATIONS

Tosti E et al., entitled "The Stress Kinase MRK Contibutes to Regulation of DNA Damage Checkpoints through a p38γ-independent Pathway," The Journal of Biological Chemistry, vol. 279, No. 46, Issue of Nov. 12, pp. 47652-47660, 2004.
Liu T-C et al., entitled "Cloning and Expression of ZAK, a Mixed Lineage Kinase-like Protein Containing a Leucine-Zipper and a Sterile-Alpha Motif," Biochemical and Biophysical Research Communications 274, 811-816, 2000.

* cited by examiner

TREATMENT OF SOLID TUMORS BY INHIBITING MRK/ZAK

CROSS-REFERENCE TO RELATED APPLICATIONS

This application is a U.S. national stage entry under 35 U.S.C. § 371 of PCT International Patent Application No. PCT/US2015/026744, filed Apr. 21, 2015, which claims the benefit of U.S. Provisional Patent Application No. 61/982,407, filed Apr. 22, 2014, the contents of which are incorporated herein by reference into the subject application.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Glioblastoma multiforme (GBM) is the most aggressive brain tumor in adults. Patients with GBM have a poor prognosis and usually survive less than 15 months following diagnosis. GBM accounts for an estimated 13,000 deaths/year in the United States. Currently, there is no effective long-term treatment for this disease. Standard of care consists of surgical removal of the tumor bulk, when possible, followed by focal radiotherapy in conjunction with temozolomide and subsequent adjuvant temozolomide. GBM is characterized by diffuse infiltration of tumor cells into the normal brain parenchyma and resistance to therapy. These two properties undermine current therapeutic efforts.

Medulloblastoma (MB) is the most common form of pediatric brain tumor, which is often accompanied by metastasis into the spinal cord. Current standard of care for MB include radio- and chemo-therapy. While the 5 year survival rate is relatively high (50-80%), the use of radiation is accompanied by severe long-term side effects, including developmental defects of the treated children.

The present invention addresses the need for improved methods and agents for treatment of solid malignant neoplastic tumors, such as glioblastoma and medulloblastoma.

SUMMARY OF THE INVENTION

Methods are provided for treating a subject with a solid tumor, such as, e.g., a glioblastoma, a medulloblastoma or a breast tumor, comprising administering to the subject a compound in an amount effective to inhibit protein kinase MRK (also known as ZAK).

A compound is provided having the structure

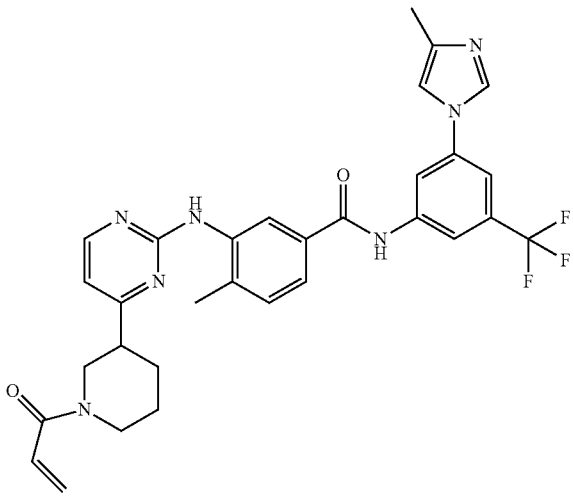 [SMILES: C=CC(=O)N1CCCC(c2ccnc(Nc3cc(C(=O)Nc4cc(-n5cnc(C)c5)cc(C(F)(F)F)c4)ccc3C)n2)C1]

or an isomer thereof, or a hydrate thereof, or a tautomer thereof, or a pharmaceutically acceptable salt thereof, or an ester prodrug thereof. The compound can act as a radiosensitizer.

The invention also provides methods for treating a subject with a solid tumor comprising administering to the subject the above compound in combination with radiation therapy, wherein the compound is administered in an amount effective to sensitize tumor cells to radiation therapy.

DETAILED DESCRIPTION OF THE INVENTION

Figure 1A:
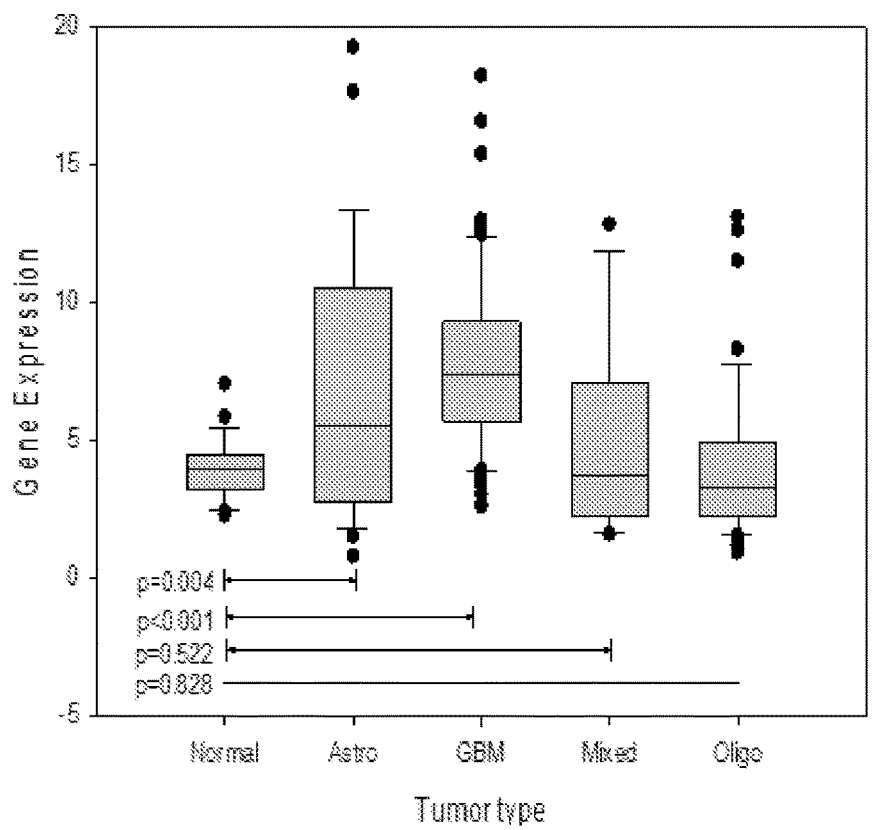
FIG. 1A. MRK expression in glioma. Gene array data from 24 normal brain samples, 29 astrocytomas, 82 GBM, 11 mixed and 49 oligodendroglioma samples. Four independent MRK probes were used.

The present invention provides a method for treating a subject with a solid tumor, such as a solid malignant neoplastic tumor, comprising administering to the subject a compound in an amount effective to inhibit protein kinase MRK. The treatment can alleviate a sign or symptom of the tumor. The treatment can inhibit the growth of the tumor. Preferably, the compound prevents or reduces tumor cell invasion. Preferably, the compound sensitizes tumor cells to radiation therapy.

The tumor can be, for example, a tumor of the brain, breast, head, neck, throat, esophagus, stomach, intestines, colon, rectum, prostate, liver, lung, kidney, pancreas, bladder or other organ. The tumor can be, for example, a glioblastoma or a medulloblastoma.

Preferably, inhibiting MRK allows the use of lower doses of radiation in patients, such as for example children with medulloblastoma. Preferably, inhibiting MRK benefits patients by preventing or reducing tumor cell invasion in, for example, medulloblastoma patients, especially e.g. those who are at risk of metastasis, or glioblastoma patients, especially e.g. those who are being treated with antiangiogenesis therapies.

In an embodiment of the methods described herein, the compound is a small molecule having a molecular weight of 2,000 daltons or less. In an embodiment of the methods described herein, the compound is a small molecule of 1,500 daltons or less. In an embodiment of the methods described herein, the compound is a small molecule of 1,000 daltons or less. In an embodiment of the methods described herein, the compound is a small molecule of 800 daltons or less. In an embodiment of the methods described herein, the compound is a small molecule of either 2000, 1500, 1000, 800, 700, 600, 500 or 400 daltons or less. In an embodiment of the methods described herein, the compound is a small organic molecule.

A preferred compound has the structure

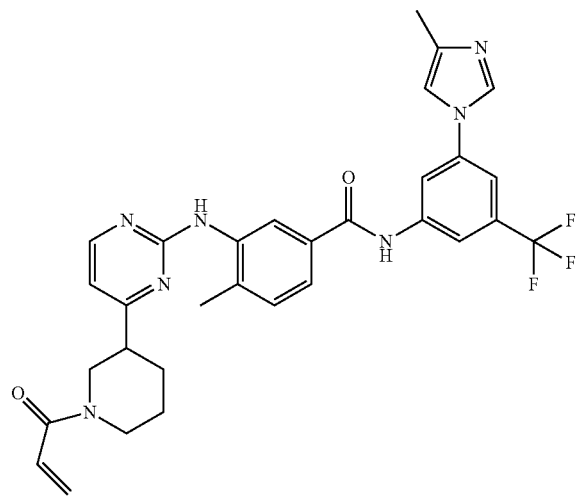 [SMILES: C=CC(=O)N1CCCC(c2ccnc(Nc3cc(C(=O)Nc4cc(-n5cnc(C)c5)cc(C(F)(F)F)c4)ccc3C)n2)C1]

or an isomer thereof, or a hydrate thereof, or a tautomer thereof, or a pharmaceutically acceptable salt thereof, or an ester prodrug thereof.

Pharmaceutically acceptable salts include non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

Preferably, the compound is a irreversible inhibitor of MRK.

The subject can be treated with a combination of the protein kinase MRK inhibitor, and radiotherapy and/or chemotherapy. Preferably, the subject is treated with ionizing radiation.

The invention also provides a compound having the structure

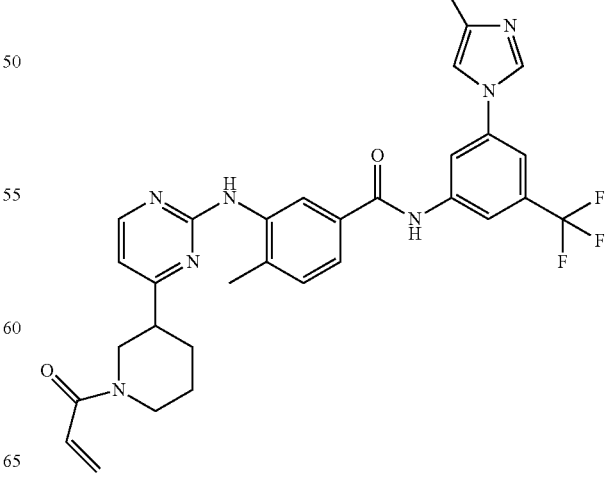

or an isomer thereof, or a hydrate thereof, or a tautomer thereof, or a pharmaceutically acceptable salt thereof, or an ester prodrug thereof.

Also provided is a pharmaceutical composition comprising the compound and a pharmaceutically acceptable carrier. A pharmaceutically acceptable carrier is a carrier that is compatible with the other ingredients of the composition without rendering the composition unsuitable for its intended purpose, and is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

Also provided is a radiosensitizer comprising the compound or the pharmaceutical composition described herein.

The invention also provides a method for treating a subject with a solid tumor, such as a solid malignant neoplastic tumor, comprising administering to the subject a compound in combination with radiation therapy, wherein the compound is administered in an amount effective to sensitize tumor cells to the radiation therapy and wherein the compound has the structure

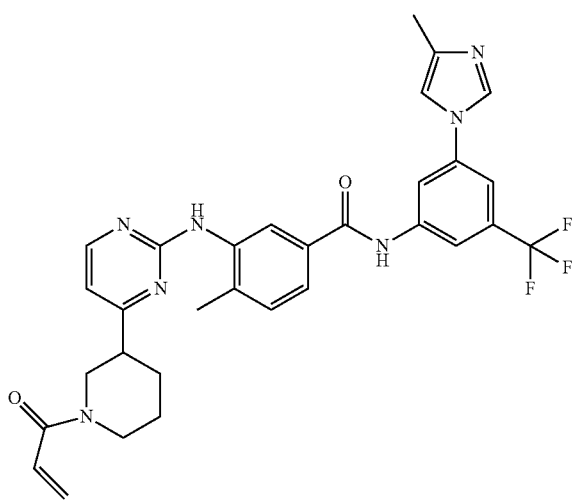 [SMILES: C=CC(=O)N1CCCC(c2ccnc(Nc3cc(C(=O)Nc4cc(-n5cnc(C)c5)cc(C(F)(F)F)c4)ccc3C)n2)C1]

or an isomer thereof, or a hydrate thereof, or a tautomer thereof, or a pharmaceutically acceptable salt thereof, or an ester prodrug thereof. Preferably, the radiation therapy comprises ionizing radiation.

The tumor can be, for example, a tumor of the brain, breast, head, neck, throat, esophagus, stomach, intestines, colon, rectum, prostate, liver, lung, kidney, pancreas, bladder or other organ. The tumor can be, for example, a glioblastoma or a medulloblastoma.

The compound can be administered as a mixture of enantiomers, such as a racemic mixture, or as a single enantiomer, i.e., a (+)enantiomer or a (−)enantiomer.

The compound can be administered to the subject by any acceptable route known in the art, including e.g. but not limited to, parenterally, intravenously, orally, intramuscularly, via an implanted reservoir, by direct injection into the tumor, or by direct injection into the tumor via an implanted reservoir. The compound can be administered by means of sustained release.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

The protein kinase MRK, also called ZAK (1), MLTK (2) and MLK7 (3), is a member of the MAP3K family of kinases that is activated by a variety of stress stimuli (4,5).

Methods and Results

MRK mRNA Levels in Glioma Patients.

Figure 1B:
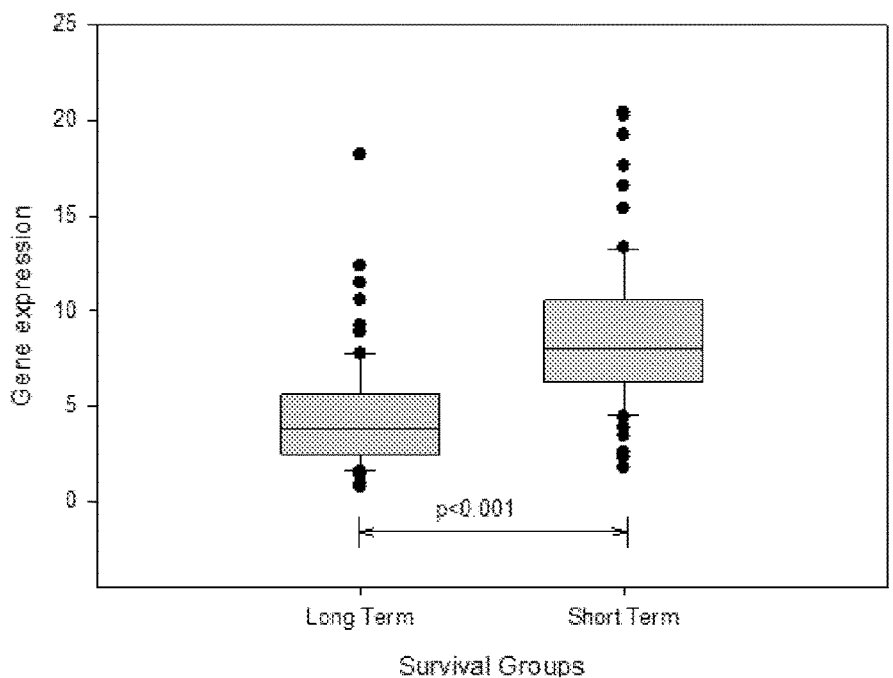
FIG. 1B. MRK expression in glioma. MRK levels were analyzed in the context of patient survival.

MRK mRNA levels increase with glioma grade and negatively correlate with patient survival (FIG. 1).

MRK Depletion Renders Cells Sensitive to Radiation.

Figure 2A:
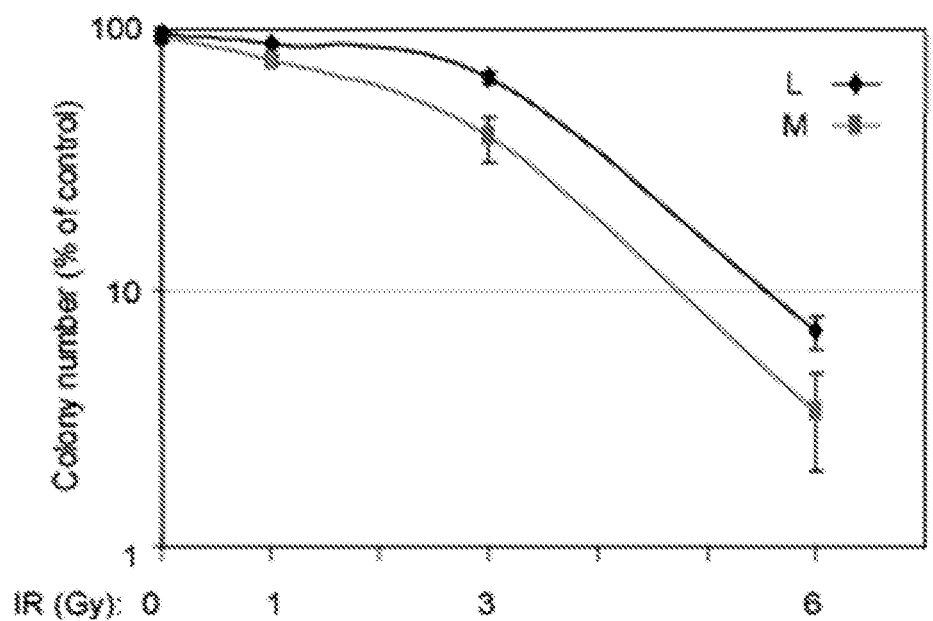
FIG. 2A. MRK down regulation sensitizes glioblastoma cells to radiation. SNB19 glioblastoma cells were transfected with luciferase (L) control or MRK (M) siRNAs and 48 hours later were seeded for the colony formation assay at 500 cells/dish. Twenty-four hours later, cells were exposed to the indicated doses of radiation and incubated at 37° C. for 7-10 days. Colonies larger than 50 cells were counted.
Figure 2B:
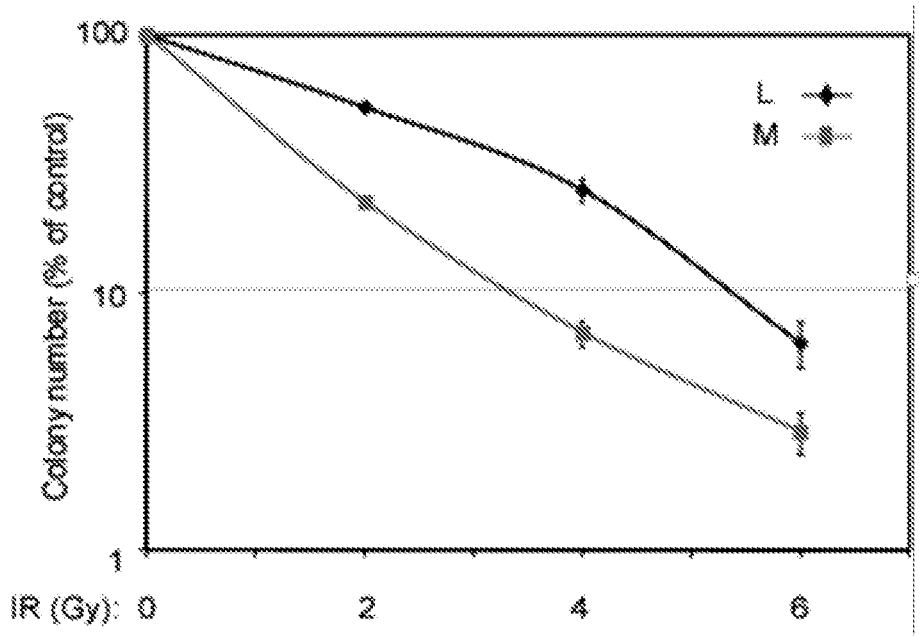
FIG. 2B. MRK down regulation sensitizes medulloblastoma cells to radiation. UW228 medulloblastoma cells were transfected with luciferase (L) control or MRK (M) siRNAs and 48 hours later were seeded for the colony formation assay at 500 cells/dish. Twenty-four hours later, cells were exposed to the indicated doses of radiation and incubated at 37° C. for 7-10 days. Colonies larger than 50 cells were counted.

MRK is activated by ionizing radiation (4,5) and is important for cell cycle arrest following DNA damage. Glioblastoma cells and medulloblastoma cells depleted of MRK are more sensitive to the killing effects of radiation than control glioblastoma and medulloblastoma cells (FIG. 2).

Effects of Down Regulation of MRK by RNA Interference on Glioblastoma Cells.

Figure 3:
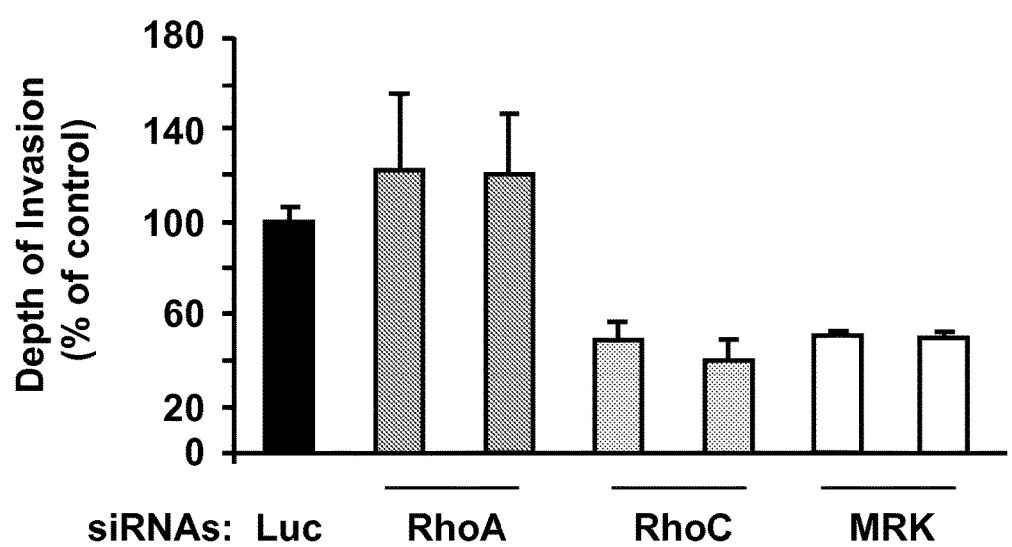
FIG. 3. MRK down regulation inhibits invasion of glioblastoma cells in rat brain slices. SNB19 glioma cells expressing GFP were transfected with small interfering RNAs directed against luciferase (control), RhoA, RhoC or MRK 2 days before implantation into the bilateral putamen on rat organotypic brain slice. Invasion rates of cells were calculated 48 hours later from Z-axis images collected by confocal laser scanning microscopy; bars are means of invasion rates±SE from six independent experiments.

MRK is activated by lysophosphatidic acid (LPA) that acts as a mitogenic and motogenic factor for tumor cells. Downstream of LPA, MRK is directly activated by RhoC, a small GTPase that is essential for tumor cell migration and invasion. Down regulation of MRK by RNA interference reduced invasion of glioblastoma cells (FIG. 3).

Figure 4:
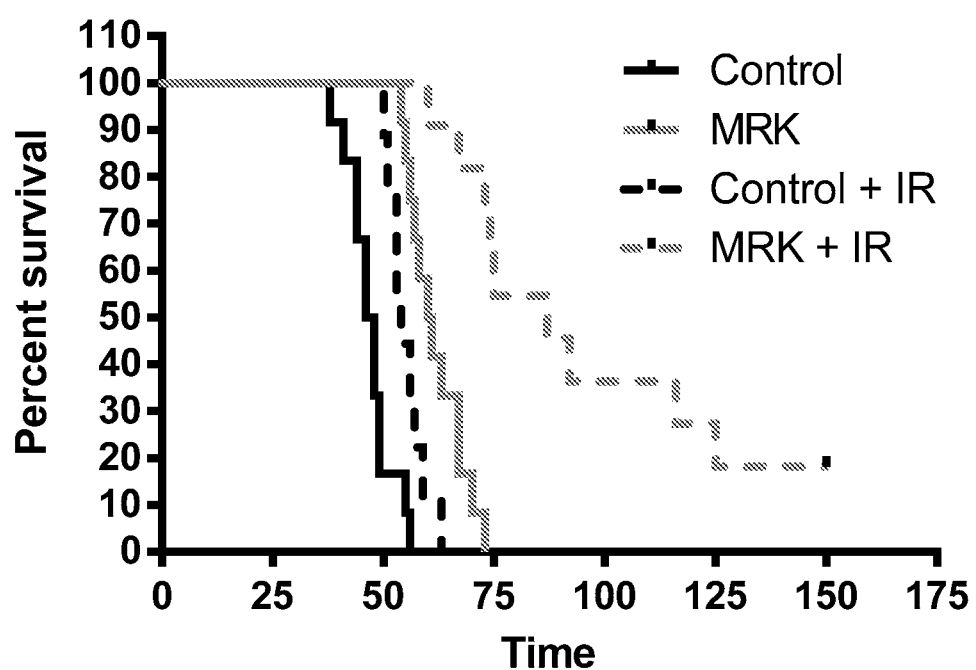
FIG. 4. Effect of MRK down regulation on animal survival. Mice carrying intracranial tumors derived from control or MRK-depleted glioblastoma cells were randomized to treatment with sham irradiation or ionizing radiation (IR) (2 Gy twice daily for 5 days). The survival for each treatment is plotted.

Down regulation of MRK by shRNA in an in vivo model of glioblastoma increased survival, which was enhanced by concomitant radiation therapy (FIG. 4). Western blot analysis of tumors of animals that became moribund revealed increased MRK expression levels compared to that of the injected cells, indicating that MRK-depleted cells were selected against in the tumor. This implies that sustained inhibition of MRK using an MRK inhibitor would have a more robust effect on animal survival.

Identification and Synthesis of a MRK Inhibitor.

A number of existing kinase inhibitors that have off-target effects on MRK were tested, and nilotinib, a c-Abl inhibitor that binds strongly to MRK (6), was identified as an MRK inhibitor of interest. Nilotinib was modified to generate a lead compound, M443. M443 was synthesized in seven steps as shown in the scheme below, and 3% overall yield was obtained.

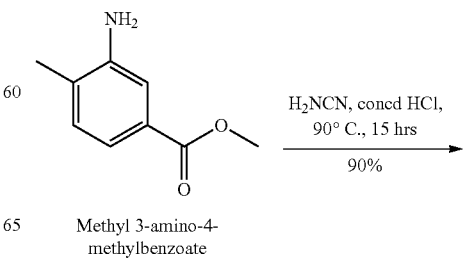

Methyl 3-amino-4-methylbenzoate

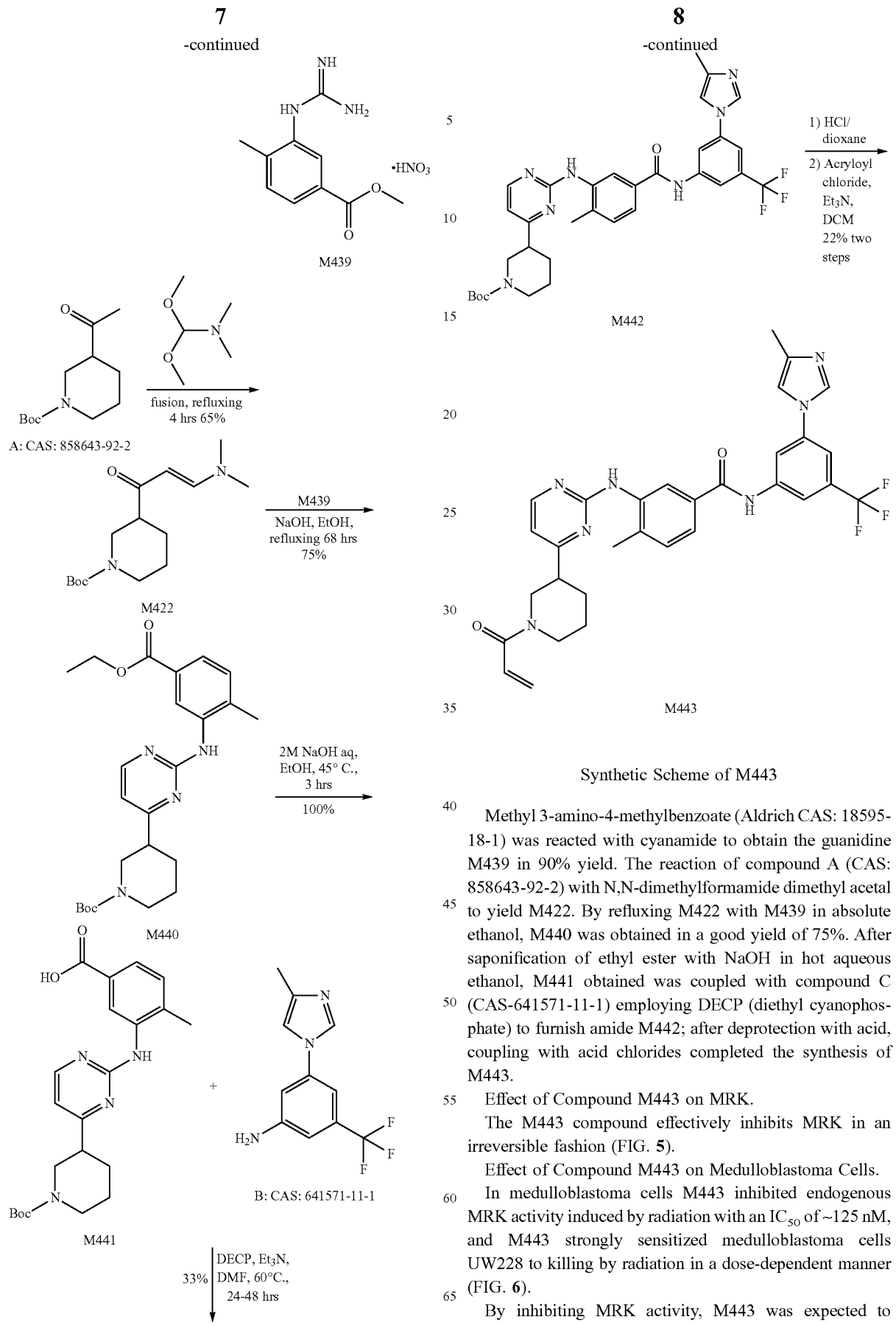

Synthetic Scheme of M443

Methyl 3-amino-4-methylbenzoate (Aldrich CAS: 18595-18-1) was reacted with cyanamide to obtain the guanidine M439 in 90% yield. The reaction of compound A (CAS: 858643-92-2) with N,N-dimethylformamide dimethyl acetal to yield M422. By refluxing M422 with M439 in absolute ethanol, M440 was obtained in a good yield of 75%. After saponification of ethyl ester with NaOH in hot aqueous ethanol, M441 obtained was coupled with compound C (CAS-641571-11-1) employing DECP (diethyl cyanophosphate) to furnish amide M442; after deprotection with acid, coupling with acid chlorides completed the synthesis of M443.

Effect of Compound M443 on MRK.

Figure 5:
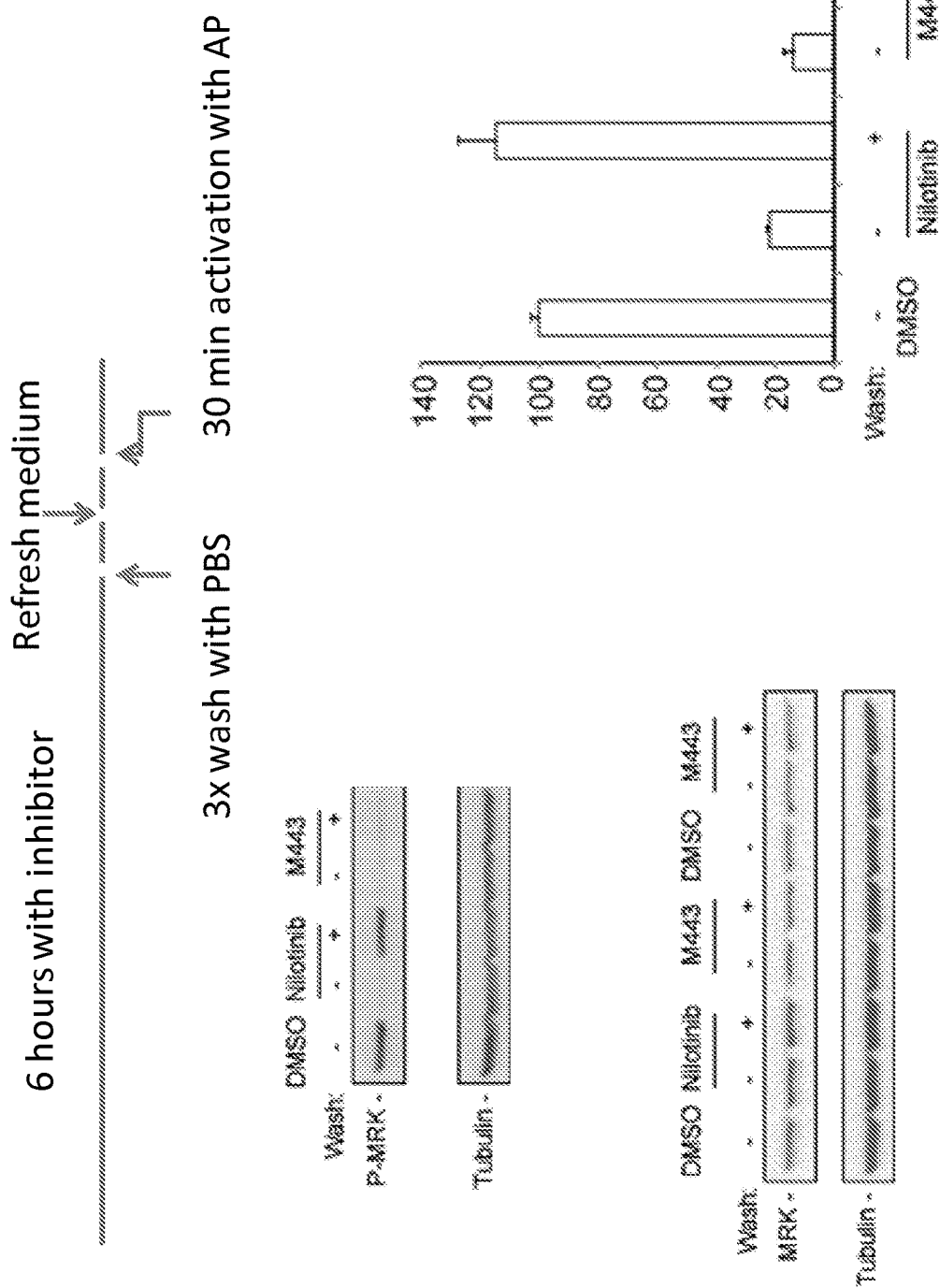
FIG. 5. M443 inhibits MRK activity in an irreversible fashion. Cells expressing an activatable MRK construct were pretreated with the indicated inhibitors for 6 hours, then they were washed with PBS 3 times, incubated for 15 minutes, washed once more and after 15 minutes they were treated with the homodimerizing drug to activate MRK. Cell lysates were western blotted with the P-MRK antibody to detect active MRK (top blot). Histograms are data from quantified P-MRK bands from three independent experiments. Bottom blot of MRK proteins shows that the inhibitors do not affect the MRK protein stability.

The M443 compound effectively inhibits MRK in an irreversible fashion (FIG. 5).

Effect of Compound M443 on Medulloblastoma Cells.

Figure 6:
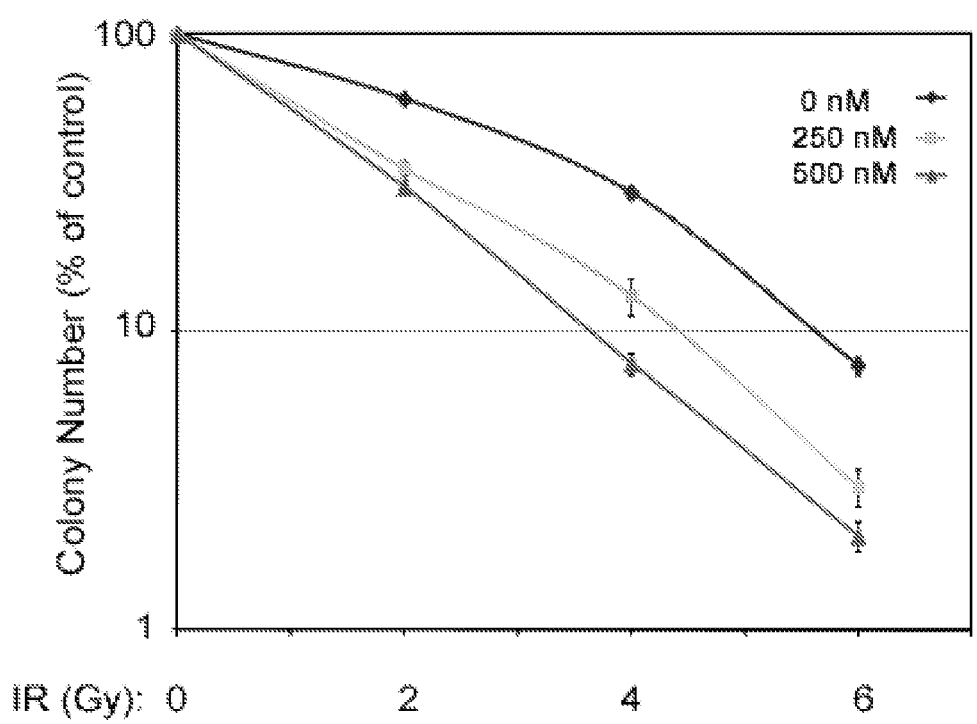
FIG. 6. M443 sensitizes UW228 medulloblastoma cells to radiation. UW228 cells were seeded for the colony formation assay at 500 cells/dish. The following day, they were treated for 6 hours with the indicated doses of M443 and then exposed to different doses of radiation. After incubation at 37° C. for 7 days, colonies larger than 50 cells were counted.

In medulloblastoma cells M443 inhibited endogenous MRK activity induced by radiation with an $IC_{50}$ of ~125 nM, and M443 strongly sensitized medulloblastoma cells UW228 to killing by radiation in a dose-dependent manner (FIG. 6).

Figure 7:
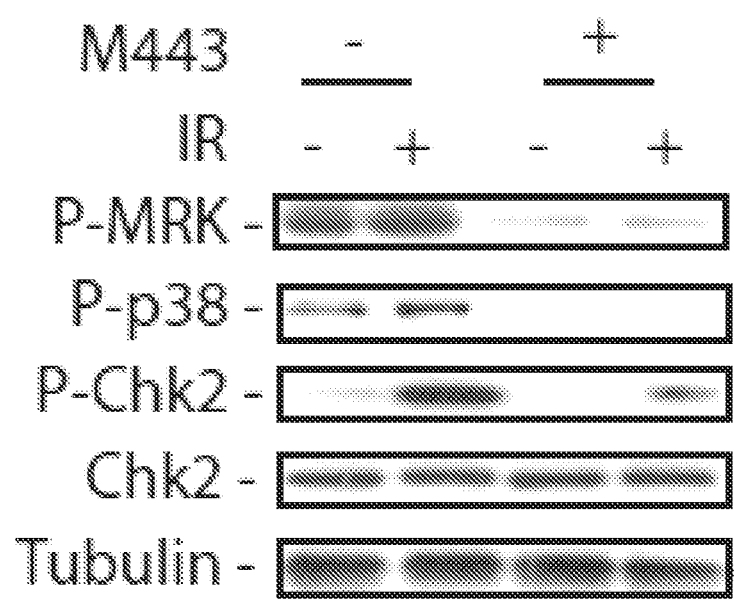
FIG. 7. Inhibition of IR-induced signaling downstream of MRK by M443. UW228 medulloblastoma cells were treated with 500 nM of M443 or with vehicle for 6 hours, and then exposed to IR or not. One hour after IR treatment, cells were harvested and cell lysates were tested by western blot for the activities of MRK, p38 and Chk2 proteins using the respective phospho-specific antibodies.

By inhibiting MRK activity, M443 was expected to reduce signal transduction downstream of MRK. FIG. 7 shows that the activation by ionizing radiation (IR) of two proteins that have been shown to be activated by MRK, Chk2 and p38, is greatly reduced after treatment with M443. Thus, M443 inhibits MRK activation by IR and its downstream signaling events, which leads to loss of cell viability after exposure to IR.

M443 as a Radiosensitizer.

Figure 8:
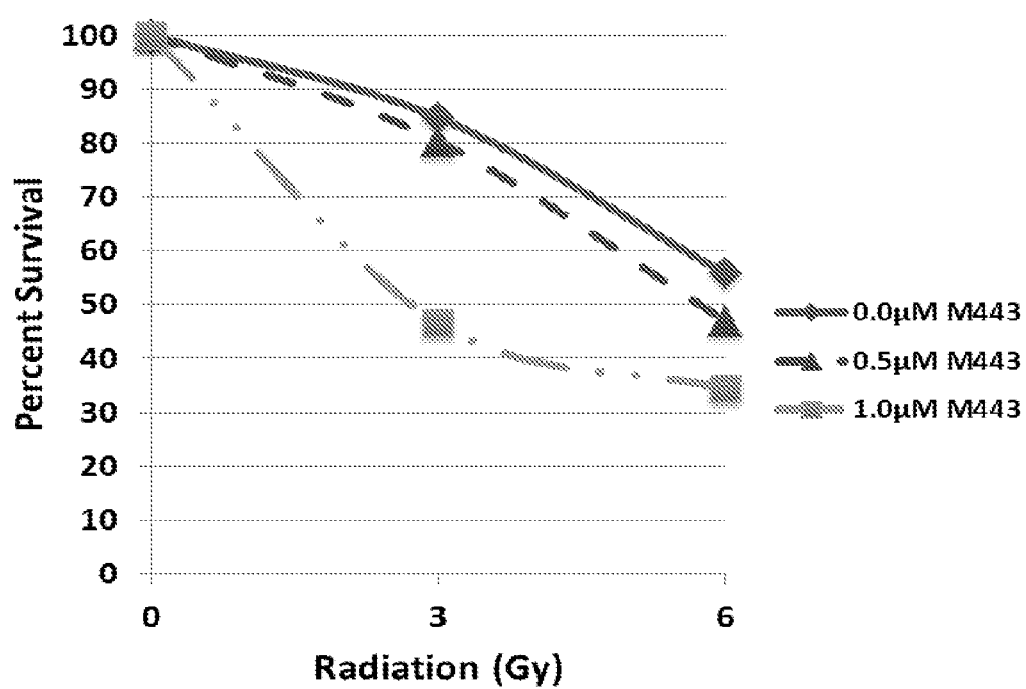
FIG. 8. M443 sensitizes breast cancer cells to X-ray irradiation. 4T1 breast cancer cells were plated in 96-well plates (750 cells per well/8 wells per condition) and treated with M443 at the indicated concentrations 6 hours before irradiating at the indicated dosages. 72 hours after irradiation MTT solution (1.25 µg/µl) was added to all wells and incubated for an additional 3 hours before cell viability/mitochondrial activity was analyzed. Shown are the means+/−SD of 8 replicate wells.

FIG. 8 shows an additional example with M443 as a radiosensitizer, where M443 sensitizes breast cancer cells to X-ray irradiation.

M443 is Effective in an Animal Model of Medulloblastoma.

Figure 9:
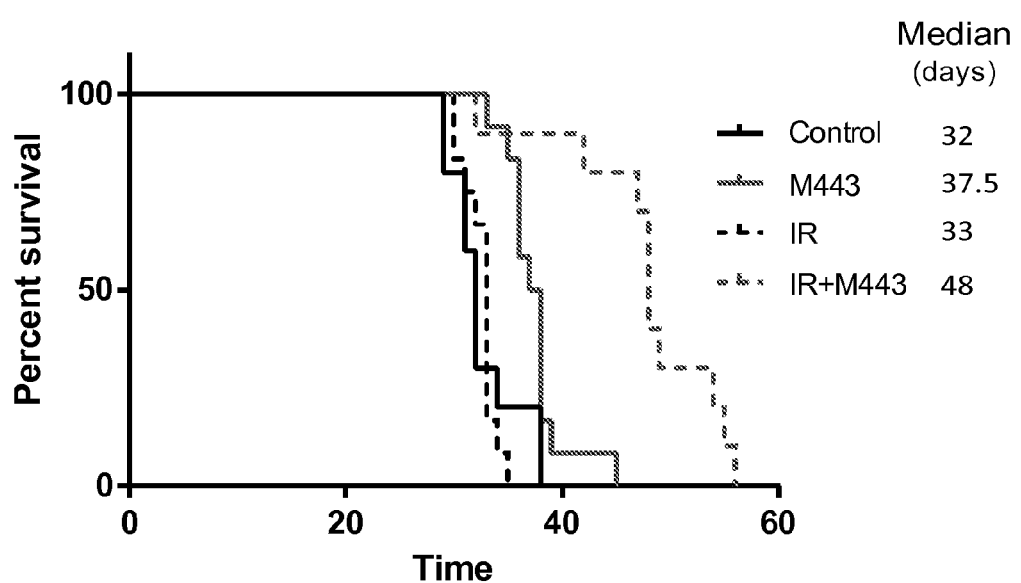
FIG. 9. Kaplan-Meier survival curve. Three weeks after implantation of IMB226 medulloblastoma cells in nude mice, animals were randomized into 4 groups of 12 mice for each treatment. M443 or the vehicle were delivered directly into the tumor via an ALZET pump.

The effect of M443 was tested in an animal model of medulloblastoma that employs orthotopic implantation of IMB226 medulloblastoma cells in nude mice. M443 was administered directly into the tumor using an osmotic pump that is connected to a catheter implanted into the brain in order to bypass the blood-brain barrier. The data shown in FIG. 9 demonstrate that M443 has a very significant radio-sensitization effect (p<0.0029, using a 2×2 factorial Cox model). While M443 and radiotherapy on their own showed very modest survival benefit, 5 days and 1 day respectively, the combination on M443 and IR showed an increase in survival of 16 days. Interestingly, the M443-treated tumors were less hemorrhagic, suggesting that M443 may also have an inhibitory effect on angiogenesis, which may contribute to its therapeutic effect.

Figure 10:
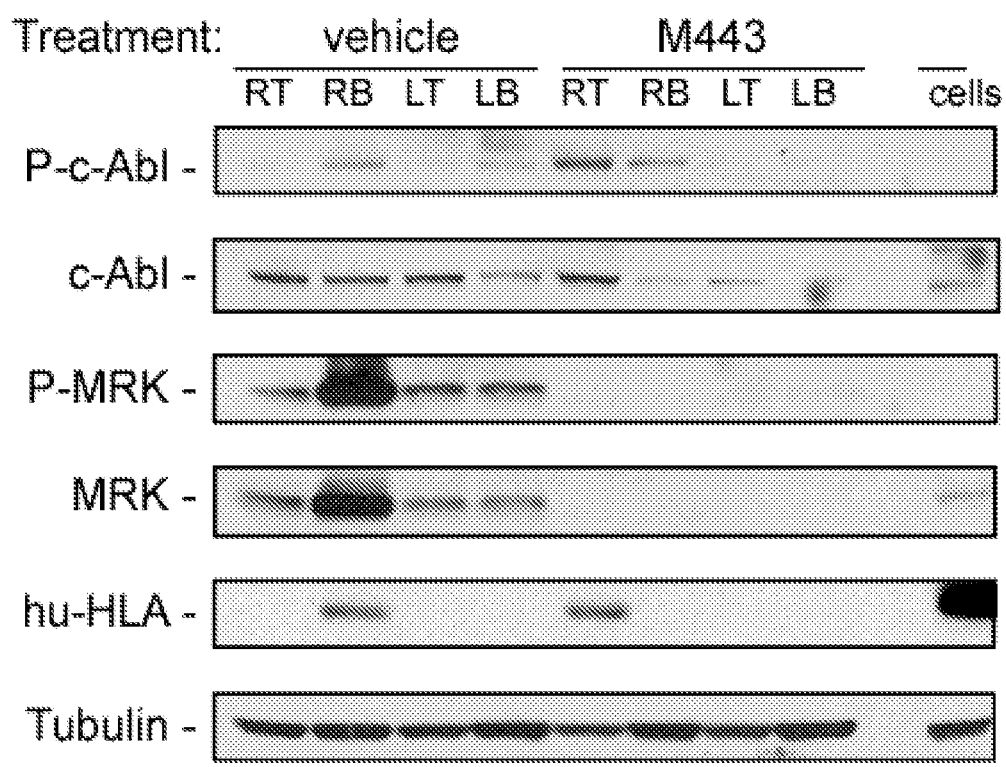
FIG. 10. Inhibition of MRK in vivo. Brains from control and M443-treated animals were harvested 18 hours after pump implantation. Each cerebellum was dissected from the rest of the brain and divided into left (L) and right (R), top (T) and bottom (B) portions. Brain lysates were tested for MRK activity by western blotting. Human HLA (hu-HLA) was used to identify the brain portions containing tumor cells of human origin. Tubulin was used as loading control.

To confirm that M443 administered into the brain inhibited MRK, brain extracts were obtained 18 hours after pump implantation, and MRK activity determined. FIG. 10 shows that lysates from vehicle-treated animal had a strong signal for total MRK protein and the corresponding phospho-MRK (P-MRK) signal, which indicates its activity, in the right bottom portion of the cerebellum (lane 2), compared with the non-tumor containing fractions (lanes 1, 3 and 4). In contrast, none of the fractions from the M443-treated animal had a detectable signal for P-MRK. The hu-HLA signal indicates the presence of tumor in the treated sample (lane 5). Remarkably, in the drug-treated tumors, total MRK levels were also strongly decreased, indicating that M443 not only deactivates but also lowers the stability of MRK, consistent with in vitro observations.

M443 Specificity.

M443 is a derivative of nilotinib, an inhibitor of the BCR-Abl oncogene. To examine the specificity of M443, the activity of c-Abl was also determined, by blotting the brain lysates with a phospho-Abl-(P-c-Abl) specific antibody. Interestingly, the P-c-Abl signal appears to be somewhat increased in the treated versus untreated tumor. As Abl is known to respond to stress, the increase in P-c-Abl may be caused by M443-induced cell stress.

Figure 11:
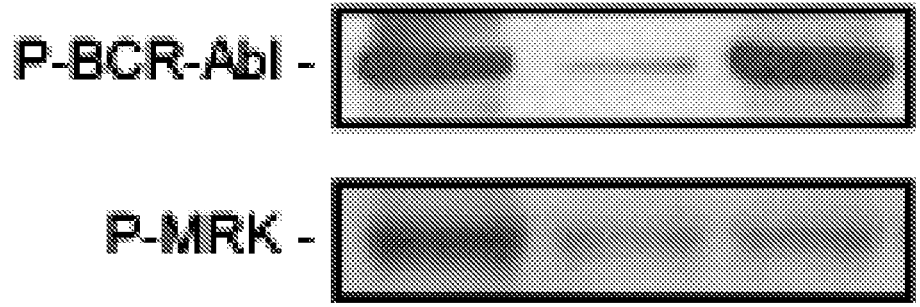
FIG. 11. M443 inhibits MRK activity, but not BCR-Abl. K562 cells were treated with DMSO, 1 µM Nilotinib or 1 µM M443 for 6 hours and then they were processed for western blot with the indicated antibodies.

To confirm that M443 has specificity for MRK and does not inhibit Abl kinase, the CML cell line K562 that expresses the constitutively active BCR-Abl fusion was used to compare the effects of M443 with those of nilotinib. FIG. 11 shows that M443 is as efficient as nilotinib at inhibiting MRK activity. In contrast, M443 does not inhibit BCR-Abl.

Discussion

Glioblastoma tumors are currently incurable. The present findings show that MRK down regulation by shRNA increases animal survival in a model of glioblastoma and that this is enhanced by radiation therapy. Thus, inhibiting MRK is expected to benefit glioblastoma patients by preventing tumor cell invasion (for example in the context of anti-angiogenic therapies that, as a side-effect, stimulate glioblastoma tumor invasiveness) and to sensitize tumor cells to radiation therapy, thereby overcoming therapeutic resistance. In addition, inhibiting MRK with the small molecule M443 radio-sensitizes medulloblastoma cells in vitro and in vivo. In the context of medulloblastoma, the use of a radio-sensitizer would allow use of lower radiation doses, while preserving therapeutic efficacy, thereby alleviating the debilitating side effects associated with the use of radiation in young adults and children. Thus, inhibition of MRK is expected to both prevent tumor cell invasion and increase the effectiveness of radiation therapy. The advantages of the irreversible MRK inhibitor M443 include strong efficacy in vivo and increased specificity, leading to less toxicity. Taken together, this study demonstrates that M443 is a good radiosensitizer of solid tumors, such as medulloblastoma and breast tumor. In addition, irreversible kinase inhibitors are thought to generate less therapeutic resistance.

REFERENCES

1. Liu, T. C., Huang, C. J., Chu, Y. C., Wei, C. C., Chou, C. C., Chou, M. Y., Chou, C. K., and Yang, J. J. (2000) Cloning and expression of ZAK, a mixed lineage kinase-like protein containing a leucine-zipper and a sterile-alpha motif. Biochem. Biophys. Res. Commun. 274, 811-816.
2. Gotoh, I., Adachi, M., and Nishida, E. (2001) Identification and characterization of a novel MAP kinase kinase kinase, MLTK. J. Biol. Chem. 276, 4276-4286.
3. Bloem, L. J., Pickard, T. R., Acton, S., Donoghue, M., Beavis, R. C., Knierman, M. D., and Wang, X. (2001) Tissue distribution and functional expression of a cDNA encoding a novel mixed lineage kinase. J. Mol. Cell Cardiol. 33, 1739-1750.
4. Gross, E. A., Callow, M. G., Waldbaum, L., Thomas, S., and Ruggieri, R. (2002) MRK, a mixed lineage kinase-related molecule that plays a role in gamma-radiation-induced cell cycle arrest. J. Biol. Chem. 277, 13873-13882.
5. Tosti, E., Waldbaum, L., Warshaw, G., Gross, E. A., and Ruggieri, R. (2004) The stress kinase MRK contributes to regulation of DNA damage checkpoints through a p38gamma-independent pathway. J. Biol. Chem. 279, 47652-47660.
6. Manley, P. W., Drueckes, P., Fendrich, G., Furet, P., Liebetanz, J., Martiny-Baron, G., Mestan, J., Trappe, J., Wartmann, M., and Fabbro, D. (2010) Extended kinase profile and properties of the protein kinase inhibitor nilotinib. Biochim. Biophys. Acta. 1804, 445-453, Epub. 2009 Nov. 14.

What is claimed is:

1. A method for treating a subject with a glioma or a medulloblastoma comprising administering to the subject a compound in an amount effective to inhibit protein kinase MRK and to sensitize the glioma or medulloblastoma to radiation therapy, wherein the compound inhibits protein kinase MRK at a dose that does not inhibit BCR-Abl.

2. The method of claim 1, wherein the compound has a molecular weight of 2,000 daltons or less.

3. A method for treating a subject with a glioma or a medulloblastoma comprising administering to the subject a compound in an amount effective to inhibit protein kinase MRK and to sensitize the glioma or medulloblastoma to radiation therapy, wherein the compound has the structure

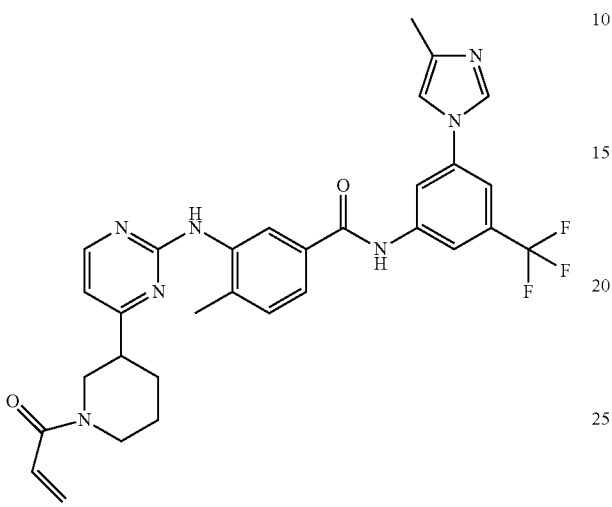

or an enantiomer or a mixture of enantiomers thereof, or a hydrate thereof, or a tautomer thereof, or a pharmaceutically acceptable salt thereof.

4. The method of claim 1, wherein the compound is an irreversible inhibitor of MRK.

5. The method of claim 1, wherein the subject is treated with a combination of the protein kinase MRK inhibitor and radiotherapy.

6. The method of claim 5, wherein the subject is treated with ionizing radiation.

7. The method of claim 1, wherein the subject has a glioblastoma.

8. The method of claim 1, wherein the subject has a medulloblastoma.

9. A compound having the structure

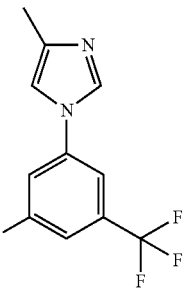

or an enantiomer or a mixture of enantiomers thereof, or a hydrate thereof, or a tautomer thereof, or a pharmaceutically acceptable salt thereof.

10. A pharmaceutical composition comprising the compound of claim 9 and a pharmaceutically acceptable carrier.

11. A radiosensitizer comprising the compound of claim 9.

12. A method for treating a subject with a glioma or a medulloblastoma comprising administering to the subject the compound of claim 9 in combination with radiation therapy, wherein the compound is administered in an amount effective to sensitize the glioma or medulloblastoma to the radiation therapy.

13. The method of claim 12 wherein the radiation therapy comprises ionizing radiation.

14. The method of claim 12, wherein the subject has a glioblastoma.

15. The method of claim 12, wherein the subject has a medulloblastoma.

16. The method of claim 1, wherein the subject has an astrocytoma.

17. The method of claim 12, wherein the subject has an astrocytoma.

* * * * *